United States Patent
Ouimette et al.

(10) Patent No.: US 10,455,835 B2
(45) Date of Patent: *Oct. 29, 2019

(54) FUNGICIDAL COMPOSITIONS FOR CONTROLLING LEAF SPOTS IN SUGAR BEETS

(71) Applicant: Dow AgroSciences LLC, Indianapolis, IN (US)

(72) Inventors: David Ouimette, Carmel, IN (US); John Todd Mathieson, Brownsburg, IN (US); Greg Kemmitt, Oxfordshire (GB)

(73) Assignee: Dow AgroSciences LLC, Indianapolis, IN (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/142,753

(22) Filed: Dec. 28, 2013

(65) Prior Publication Data

US 2014/0187589 A1  Jul. 3, 2014

Related U.S. Application Data

(60) Provisional application No. 61/747,496, filed on Dec. 31, 2012.

(51) Int. Cl.
*A01N 43/40* (2006.01)

(52) U.S. Cl.
CPC .................... *A01N 43/40* (2013.01)

(58) Field of Classification Search
CPC ..................................................... A01N 43/40
USPC .......................................................... 514/336
See application file for complete search history.

(56) References Cited

U.S. PATENT DOCUMENTS

| 5,276,038 A | 1/1994 | Takasugi et al. |
| 6,953,807 B2 | 10/2005 | Hutin et al. |
| 2004/0110777 A1 | 6/2004 | Annis et al. |
| 2004/0192924 A1* | 9/2004 | Meyer ............ A01N 43/40 546/281.7 |
| 2011/0082160 A1 | 4/2011 | Owen et al. |

FOREIGN PATENT DOCUMENTS

| WO | 2003035617 A1 | 5/2003 |
| WO | 2011044213 A1 | 4/2011 |

OTHER PUBLICATIONS

PCT/US2013/078505 filed Dec. 31, 2013, International Search Report dated Apr. 24, 2014.

\* cited by examiner

*Primary Examiner* — Melenie L Gordon
*Assistant Examiner* — Taina D Matos Negron
(74) *Attorney, Agent, or Firm* — Hunton Andrews Kurth LLP

(57) ABSTRACT

A new method for the control and prevention of sugar beet leaf spot caused by *Cercospora beticola* (CERCBE) in a sugar beet plant has been discovered. The method involves applying effective amounts of Formula I to sugar beets.

5 Claims, No Drawings

FUNGICIDAL COMPOSITIONS FOR CONTROLLING LEAF SPOTS IN SUGAR BEETS

CROSS-REFERENCE TO RELATED APPLICATIONS

This application claims the benefit of U.S. Provisional Patent Application Ser. No. 61/747,496 filed Dec. 31, 2012, which is expressly incorporated by reference herein.

FIELD OF THE INVENTION

This invention concerns a new method for controlling leaf spot in sugar beets with a fungicidally effective amount of a compound of Formula I.

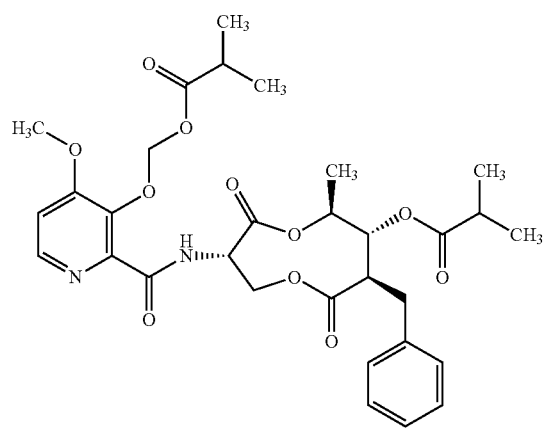

(1)

BACKGROUND AND SUMMARY OF THE INVENTION

Sugar beets are grown commercially for a wide variety of purposes including for sugar production. Leaf spot, caused by a fungus (*Cercospora beticola*) is one disease that often attacks sugar beet crops. The fungus is usually characterized by black, pycnidia containing, concentric circles. The fungus often eventually leads to necrosis of the leaf tissue. Failures of entire sugar beet crops have resulted directly from sugar beet leaf spot epidemics. There is a need for additional and/or more effective agents for protecting plants, including sugar beets, from damage caused by this pathogen.

Fungicides are compounds, of natural or synthetic origin, which act to protect plants against damage caused by fungi. Current methods of agriculture rely heavily on the use of fungicides. In fact, some crops cannot be grown usefully without the use of fungicides. The use of fungicides allows a grower to increase the yield and the quality of the crop and consequently, increase the value of the crop. In most situations, the increase in value of the crop is worth at least three times the cost of the use of the fungicide.

There are a number of fungicides used to control sugar beet leaf spot. These include both azoxtstrobin and difenconazole. Azoxtstrobin is the common name for methyl (αE)-2-[[6-(2-cyanophenoxy)-4-pyrimidinyl]oxy]-α-(methoxymethylene)benzeneacetate. Difenconazole is the common name for 1H-1,2,4-Triazole, 1-((2-(2-chloro-4-(4-chlorophenoxy)phenyl)-4-methyl-1,3-dioxolan-2-yl)methyl)-. Their fungicidal activity is described in *The Pesticide Manual*, Fourteenth Edition, 2006.

Unfortunately, in some cases known fungicides for leaf spot are not effective enough or may have other deleterious effects. Accordingly, it would be useful to discover new methods of controlling leaf spot in sugar beet crops.

Advantageously, a new method has been discovered. In one embodiment the present invention pertains to a new method for the control and prevention of sugar beet leaf spot caused by *Cercospora beticola* (CERCBE) in a sugar beet plant. The method comprises: applying a fungicidally effective amount of a compound of Formula I.

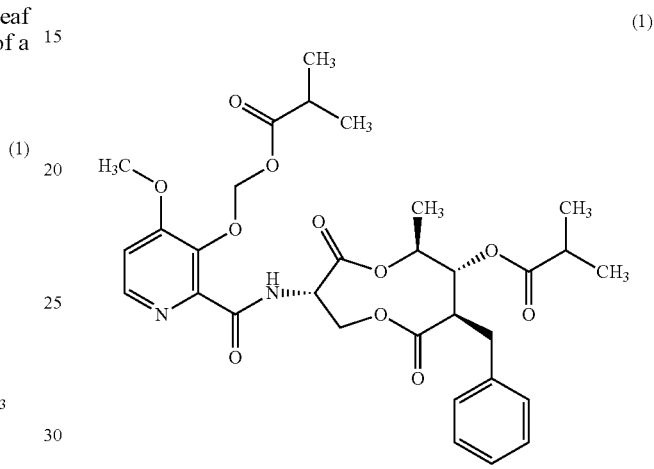

(1)

The effective amount is applied to at least one of the plant, an area adjacent to the plant, soil adapted to support growth of the plant, a root of the plant, foliage of the plant, and a seed adapted to produce the plant.

DETAILED DESCRIPTION OF THE INVENTION

The present invention concerns applying a fungicidally effective amount of a compound of Formula I

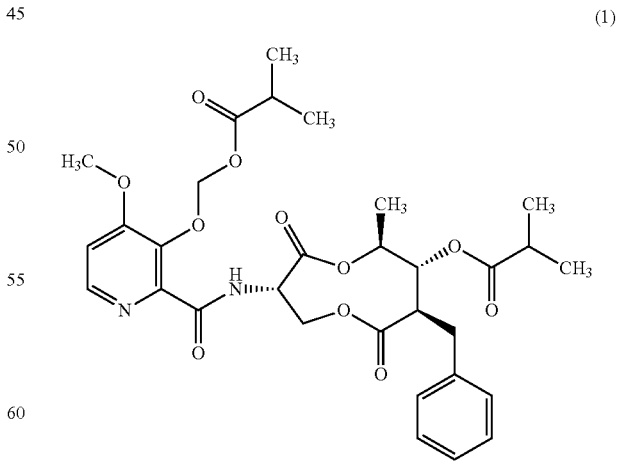

(1)

The effective amount is applied to at least one of the plant, an area adjacent to the plant, soil adapted to support growth of the plant, a root of the plant, foliage of the plant, and a seed adapted to produce the plant.

As used herein, the term "fungicidally effective amount" is synonymous with the phrase "amount effective to control or reduce fungi" and is used in relation to a fungicidal composition in an amount that will kill or materially inhibit the growth, proliferation, division, reproduction, or spread of fungus.

The rate at which compound of Formula I is applied will depend upon the specific composition, particular type of fungus to be controlled, the degree of control required and the timing and/or the method of application. In general, the fungicidally effective amount of a compound of Formula I may comprise applying a composition comprising Formula I, i.e, Formula I composition, to a crop of sugar beets at an application rate of at least about 50, or at least about 60, or at least about 75, or at least about 90, or at least about 100 grams per hectare (g/ha). On the other hand. the fungicidally effective amount of a compound of Formula I may comprise applying it at an application rate of up to as much as about 2300, or as much as about 800, or as much as about 300, or as much as about 250, or as much as about 200 g/ha based on the total amount of active ingredients in the composition. Often, the compound of Formula I may be applied at a rate between about 100 g/ha and about 300 g/ha.

The Formula I composition of the present invention can be applied either alone or as part of a multipart fungicidal system. When part of a multipart system, the Formula I composition can be applied in conjunction with one or more other fungicides to control a wider variety of undesirable diseases. When used in conjunction with other fungicide(s), Formula I may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compound of Formula I may be applied in a form with a phytologically acceptable carrier if desired.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of the antifungal composition.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present invention contemplates all vehicles by which the compound of Formula I can be formulated for delivery and use as a fungicide in the present methods.

As will be readily appreciated, any material to which the composition comprising Formula I can be added may be used, provided they yield the desired utility without significant interference with the activity as antifungal agent.

Wettable powders, which may be compacted to form water dispersible granules, comprise an intimate mixture of the composition of Formula I, a carrier and agriculturally acceptable surfactants. The concentration of the composition in the wettable powder is usually from about 10% to about 90% by weight, more preferably about 25% to about 75% by weight, based on the total weight of the formulation. In the preparation of wettable powder formulations, the composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the Formula I composition comprise a convenient concentration, such as from about 10% to about 50% by weight, in a suitable liquid, based on the total weight of the emulsifiable concentrate formulation. The components of the composition, jointly or separately, are dissolved in a carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the Formula I composition. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the Formula I component, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The Formula I composition may also be applied as granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the Formula I composition in a suitable solvent and applying it to a granular carrier which has been preformed to the appropriate particle size, in the range of from about 0.5 to about 3 mm. Such formulations may also be prepared by making a dough or paste of the carrier and the Formula I composition, and crushing and drying to obtain the desired granular particle.

Dusts containing the Formula I composition are prepared simply by intimately mixing the Formula I composition in powdered form with a suitable dusty agricultural carrier, such as, for example, kaolin clay, ground volcanic rock, and the like. Dusts can suitably contain from about 1% to about 10% by weight of the Formula I composition/carrier combination.

The formulations may contain agriculturally acceptable adjuvant surfactants to enhance deposition, wetting and penetration of the Formula I composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that can comprise at least 1% by weight of one or more of the Formula I compositions with another pesticidal compound. Such additional pesticidal compounds may be fungicides, insecticides, nematocides, miticides, arthropodicides, bactericides or combinations thereof that are compatible with the Formula I compositions of the present invention in the medium selected for application, and not antagonistic to the activity of the present compounds. Accordingly, in such embodiments the other pesticidal compound is employed as a supplemental toxicant for the same or for a different pesticidal use. The pesticidal compound and the Formula I composition can generally be mixed together in a weight ratio of from 1:100 to 100:1.

The present invention includes within its scope methods for the control or prevention of fungal attack. These methods comprise applying to the locus of the fungus, or to a locus in which the infestation is to be prevented (for example applying to sugar beet plants), a fungicidally effective amount of the Formula I composition. The Formula I composition is suitable for treatment of various plants at fungicidal levels, while exhibiting low phytotoxicity. The Formula I composition is useful in a protectant or eradicant fashion. The Formula I composition may be applied by any of a variety of known techniques, either as the Formula I composition or as a formulation comprising the Formula I composition. For example, the Formula I compositions may be applied to the roots, seeds or foliage of plants for the control of various fungi, without damaging the commercial value of the plants. The Formula I composition may be applied in the form of any of the generally used formulation types, for example, as solutions, dusts, wettable powders, flowable concentrates, or emulsifiable concentrates. These materials are conveniently applied in various known fashions.

The Formula I composition has been found to have significant fungicidal effect particularly for agricultural use. The Formula I composition is particularly effective for use with agricultural crops and horticultural plants. In particular, the Formula I compositions are capable of preventing or curing, or both, sugar beet leaf spot caused by, for example, *Cercospora beticola*. Similarly, the Formula I compositions are sometimes capable of preventing or curing, or both, other diseases caused by a wide range of fungi including, for example, *Basidiiomycetes* and/or *Ascomycetes*.

The Formula I compositions have a broad range of efficacy as a fungicide. The exact amount of the Formula I composition to be applied is dependent not only on the relative amounts of the components, but also on the particular action desired, the specific fungi to be controlled, and the stage of growth thereof, as well as the part of the plant or other product to be contacted with the Formula I composition. Thus, formulations containing the Formula I composition may not be equally effective at similar concentrations or against the same fungal species.

The Formula I compositions are effective in use with plants in a disease inhibiting and phytologically acceptable amount. The term "disease inhibiting and phytologically acceptable amount" refers to an amount of the Formula I composition that kills or inhibits the plant disease for which control is desired, but is not significantly toxic to the plant. This amount will generally be from about 1 to about 1000 ppm, with about 2 to about 500 ppm being preferred. The exact concentration of Formula I composition required varies with the fungal disease to be controlled, the type of formulation employed, the method of application, the particular plant species, climate conditions, and the like. A suitable application rate for the Formula I composition typically corresponds to about 0.10 to about 4 pounds/acre (about 0.1 to 0.45 grams per square meter $g/m^2$).

The present compositions can be applied to fungi or their locus by the use of conventional ground sprayers, granule applicators, and by other conventional means known to those skilled in the art.

The following examples are provided to further illustrate the invention. They are not meant to be construed as limiting the invention.

EXAMPLES

Evaluation of Protectant Activity of Fungicide Mixtures vs. sugar beet leaf spot caused by *Cercospora beticola* (CERCBE). Sugar beet plants (variety 'HH88') were grown in soil-less Metro mix and trimmed regularly to maintain an uniform plant size prior to test. To prepare inoculum, dried diseased beet leaves were placed in a moist chamber overnight to promote sporulation. Spores were rinsed off leaves with distilled water, filtered through cheesecloth to remove plant debris, then adjusted to $4\times10^4$ spores/ml. Tween 20 was added at 3 drops per 100 ml. Sugar beet seedlings were inoculated 3 days prior to or 4 to 5 days after fungicide treatments. Inoculated plants were kept in a dew chamber at 22° C. for 48 hr then incubated in a greenhouse set at 24° C. under a clear plastic hood until disease symptoms were fully expressed. Disease severity was assessed on both treated and untreated plants.

The following fungicides were used for an efficacy example:

| Chemical Name | Trade name | Formulation |
| --- | --- | --- |
| Formula I | Not applicable | SC (13.3%) |
| azoxystrobin | AMISTAR ™ | SC (25.0%) |
| difenconazole | INSPIRE SUPER MP ™ | EC (23.2%) |

The efficacy of various formulations is shown in the table below wherein the values are percent disease severity. Results of the factorial analysis across all rates and replicates. Values with the same letter are not significantly different (P=0.05).

| Treatment | Ex. 1 3DC | Ex. 2 5DP | Ex. 3 3DC | Ex. 4 4DP | Ex. 5 3DC |
| --- | --- | --- | --- | --- | --- |
| Formula I + Trycol 5941 (0.1% v/v) | 23.1 a | 6.6 a | 5.2 a | 6.4 ab | 7.2 b |
| QUADRIS ™ (azoxystrobin) | 3.2 b | 3.0 b | 3.2 b | 3.8 b | 3.8 bc |

-continued

| Treatment | Ex. 1 3DC | Ex. 2 5DP | Ex. 3 3DC | Ex. 4 4DP | Ex. 5 3DC |
|---|---|---|---|---|---|
| difenconazole | 1.2 b | 2.2 b | 0.6 c | 2.5 b | 0.4 c |
| untreated disease severity | 23.0 | 31.0 | 48.0 | 35.0 | 26.0 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for the control and prevention of sugar beet leaf spot caused by *Cercospora beticola* (CERCBE) in a sugar beet plant, the method consisting essentially of: applying a fungicidally effective amount of a compound of Formula I, wherein the compound of Formula I is applied at a rate between about 100 g/ha and about 300 g/ha, and wherein said effective amount is applied to the plant 2. The method of claim 1 wherein the compound of Formula I is dispersed within an agriculturally acceptable adjuvant or carrier.

3. The method of claim 1 wherein the compound of Formula I is dispersed within an agriculturally acceptable adjuvant surfactant selected from the group consisting of ethoxylated nonyl phenols, ethoxylated synthetic or natural alcohols, salts of the esters or sulphosuccinic acids, ethoxylated organosilicones, ethoxylated fatty amines, and mixtures thereof.

4. The method of claim 3 wherein the compound of Formula I is dispersed from 0.01 percent to 1.0 percent v/v based on a spray-volume of water of an agriculturally acceptable adjuvant surfactant.

5. A method of inhibiting the growth of sugar beet leaf spot caused by *Cercospora beticola* (CERCBE) in a sugar beet plant, the method comprising: applying an amount of a compound of Formula I to a sugar beet plant, wherein the amount of a Formula I applied is an amount that will materially inhibit the growth of CERCBE, and wherein the compound of Formula I is applied at a rate between about 100 g/ha and about 300 g/ha

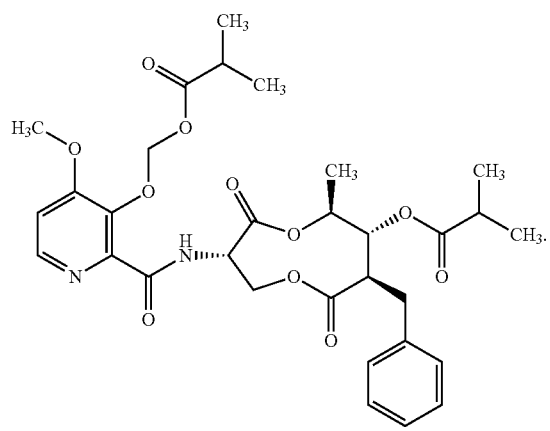

(1)

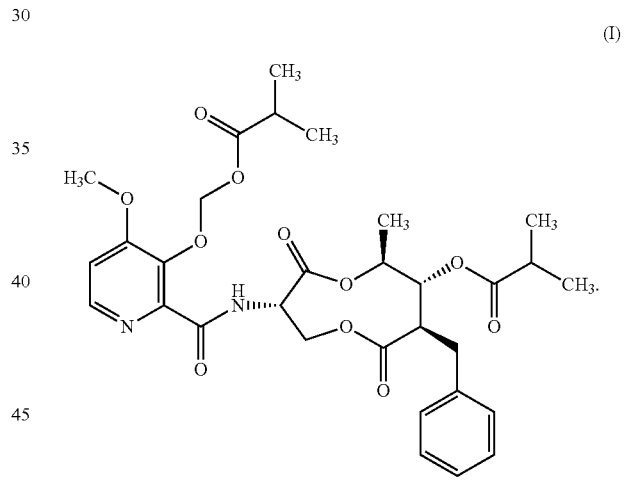

(I)

* * * * *